United States Patent [19]
Sivard

[11] Patent Number: 5,807,144
[45] Date of Patent: Sep. 15, 1998

[54] DEVICE FOR AFFIXING A LEAD CONNECTOR TO AN IMPLANTABLE STIMULATOR

[75] Inventor: Ake Sivard, Solna, Sweden

[73] Assignee: Pacesetter AB, Solna, Sweden

[21] Appl. No.: 786,570

[22] Filed: Jan. 21, 1997

[30] Foreign Application Priority Data

Jan. 29, 1996 [SE] Sweden .................................. 9600311

[51] Int. Cl.⁶ ..................................................... H01R 4/48
[52] U.S. Cl. ......................... 439/816; 439/909; 439/819; 439/820; 607/37
[58] Field of Search ................................ 607/36, 37, 115, 607/116; 439/909, 816, 819, 820, 824, 825–827, 700, 461, 462, 460, 345, 346

[56] References Cited

U.S. PATENT DOCUMENTS

| | | |
|---|---|---|
| 5,069,209 | 12/1991 | Posin .......................................... 607/37 |
| 5,086,773 | 2/1992 | Ware . |
| 5,378,177 | 1/1995 | Froeberg et al. . |
| 5,507,662 | 4/1996 | Nyman . |

FOREIGN PATENT DOCUMENTS

| | | | |
|---|---|---|---|
| 0 590 756 | 6/1994 | European Pat. Off. . | |
| 2411612 | 7/1979 | France ...................................... | 607/37 |

*Primary Examiner*—Jeffrey R. Jastrzab
*Attorney, Agent, or Firm*—Hill & Simpson

[57] ABSTRACT

A device for affixing an elongate contact pin on an electrode lead for connection to a medical implant, such as a heart stimulator, contains an elongate connector part with an opening at one end into which the contact pin can be inserted. The connector part has an affixing part which, when acted on by the contact pin, can move in the connector part's longitudinal direction between a contact pin-affixing position and a contact pin-release position.

8 Claims, 4 Drawing Sheets

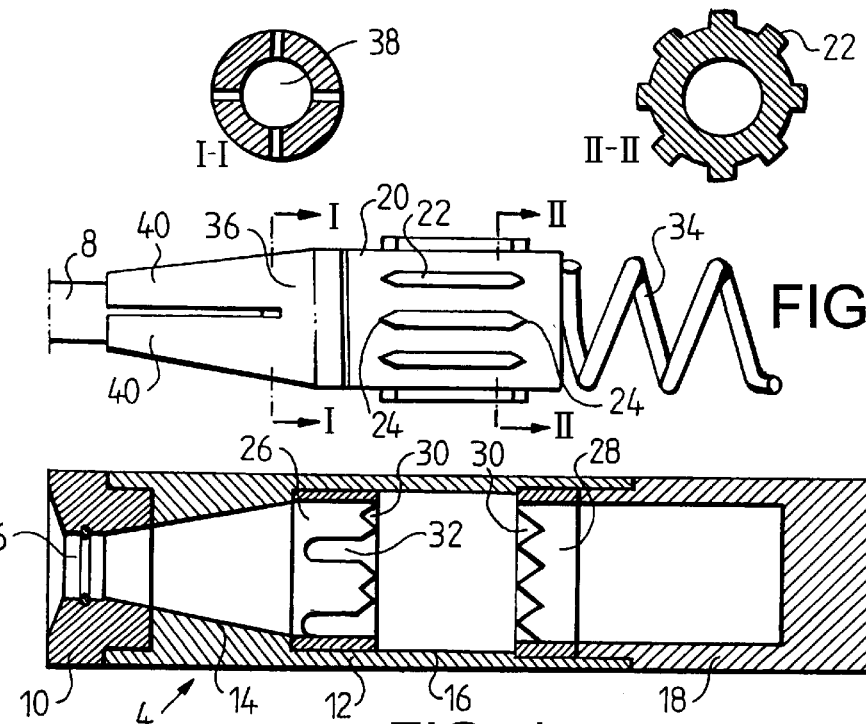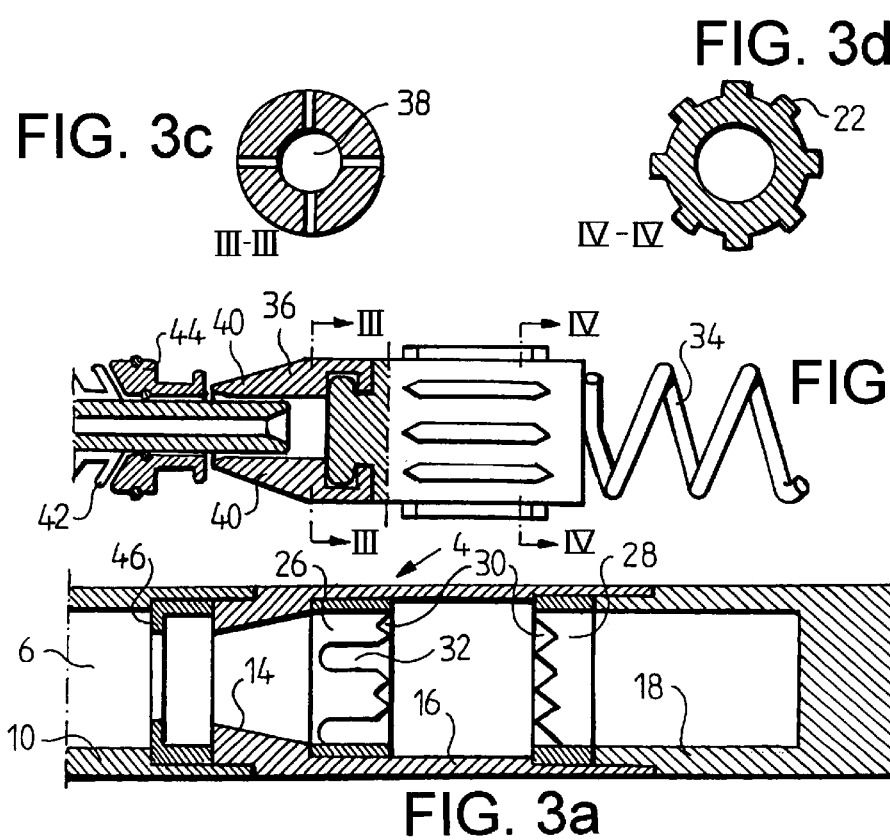

DEVICE FOR AFFIXING A LEAD CONNECTOR TO AN IMPLANTABLE STIMULATOR

BACKGROUND OF THE INVENTION

1. Field of the Invention

The present invention is directed to a device for affixing a connector at one end (usually referred to as the "proximal end") of a lead to an electrical stimulation device having a connector receptacle, and in particular to a device for affixing the proximal end of a medical electrode lead to an implantable stimulator, such as a pacemaker, cardioverter or defibrillator.

2. Description of the Prior Art

The connecting part of a pacemaker or other medical stimulator often is formed by a molded-on section containing an electrode connection terminal, the molded-on section being made of transparent epoxy plastic mounted on the exterior of the pacemaker enclosure. The electrode connection terminals in the molded-on section are in electrical contact with the pacemaker circuits in the enclosure via a number of connection pins. The proximal end of the electrode cable has a contact pin which is secured inside the molded-on section e.g. with screws. In the description of the prior art in U.S. Pat. No. 5,086,773 examples of such solutions are discussed. The device described in that patent is an example of a way the contact pin can be affixed without the need for screws or tools. The locking device described in that patent contains a coil spring arranged in a connection socket for affixing the contact pin. The internal diameter of the coil spring is somewhat smaller than the external diameter of the contact pin. When the contact pin is rotated part of one turn in the coil spring's uncoiling direction at the same time as the contact pin is pushed into the connection socket, the spring expands enough to allow the contact pin to be pushed into the spring. When the contact pin is released, the spring strives to return to its normal position, thereby gripping the contact pin and affixing the contact pin on the electrode cable. One problem with this prior known device is that the spring could be broken if the contact pin, secured by the locking device, is mistakenly rotated in the spring's coiling direction, i.e. opposite to the spring's uncoiling direction.

Another device for affixing an electrode cable in a connection means on a heart stimulator is described in European Application 0 590 756. This known affixing device has a spring plate, molded inside the connection means, with opposed resilient, clamping tongues designed to grip the cable's contact pin to prevent the end of the electrode cable from being pulled out of the connection means, the retention force of the clamp increasing when a withdrawal force is exerted on the electrode cable. The grip of the clamping tongues on the contact pin on the end of the cable loosens when pressure is applied to opposed, projecting lateral tabs on the spring plate. A problem with this known device is that the contact pin could be released by mistake if pressure is applied to the lateral tabs.

SUMMARY OF THE INVENTION

An object of the present invention is to provide an improved affixing device which does not require any tool to achieve affixing and which cannot be released by the application of clamping on the connection means.

The above object is achieved in accordance with the principles of the present invention in a device for affixing a lead connector, in the form of an elongate contact pin, of an electrode lead to an implantable stimulator, wherein the device has an elongate connector part with an opening at one end through which the contact pin can be inserted into the connector part, and having an affixation assembly arranged in the connector part which, when acted on by the contact pin by movement thereof in the longitudinal direction of the connector part, moves between a contact pin-affixing position and a contact pin-release position. The contact pin passes through the affixing assembly as it is inserted into the connector part along the aforementioned longitudinal direction of the connector part.

In accordance with the invention, affixing of a contact pin to a connector part is therefore achieved by the incorporation of an affixing part, inside the connector part, which is able to move in the connector part's longitudinal direction, when force is applied to the contact pin, between a contact pin-affixing position and a contact pin-release position.

The affixing part is spring-loaded and pushes against the contact pin, securing it when the affixing part is in its affixing position. When a force is applied to the contact pin and the pin is pushed in the contact pin's longitudinal direction towards the connector part, the affixing part's force-applying components are released and the contact pin can then be withdrawn from the connector part.

When the contact is to be secured in the connector part, the contact pin is pushed with a predetermined force a predetermined distance into the connector part in the contact pin's longitudinal direction, the pin then being secured, when released, as the affixing part assumes its affixing position.

The invention relates to the affixing of a contact pin for an electrode lead intended for connection to a medical implant, for example a pacemaker or defibrillator. A general requirement in the design of these implants is for them to be as small as possible. A pacemaker of the latest generation of pacemakers only weighs 14 grams. A standard type of contact pin for connecting an electrode lead to a pacemaker has an external diameter of 1.62 mm. This gives an idea of the size of the affixing device.

As noted above, contemporary pacemakers have a molded-on epoxy section into which the electrode lead is connected.

According to the invention connection will instead be made directly into the pacemaker enclosure through a "black hole" without affixing screws. The affixing device is inside the pacemaker enclosure. This solution means that the molded-on section currently employed will not be needed to achieve lead connection.

According to a first preferred embodiment of the invention, the affixing device has a connector part containing a cylindrical guide body, pressing against a main spring acting on the affixing part and movably arranged in the connector part, with rib-like, longitudinal projections on the surface of the guide body. The connector part further contains an inner and outer tubular guide arranged to interact with the tips of the longitudinal projections when there is a shift between the contact pin-affixing position and contact pin-releasing position.

According to a second preferred embodiment of the invention, the affixing device has a connector part containing an upper and a lower blocking part with a first and a second blocking tab on each blocking part to interact with the affixing part when there is a shift between the contact pin-affixing position and the contact pin releasing position.

DESCRIPTION OF THE DRAWINGS

FIG. 1a shows a connector part of a first embodiment of the invention.

FIG. 1b shows an affixing assembly contained in the connector part of FIG. 1a in the first embodiment.

FIG. 1c shows a cross section along line I—I of FIG. 1b.

FIG. 1d shows a cross section along line II—II of FIG. 1b.

FIG. 3a shows a connector part of a second embodiment of the invention.

FIG. 3b shows an affixing assembly contained in the connector part of FIG. 3a in the second embodiment.

FIG. 3c shows a cross section along line III—III of FIG. 3b.

FIG. 3d shows a cross section along line IV—IV of FIG. 3b.

DESCRIPTION OF THE PREFERRED EMBODIMENTS

Figure 2A:
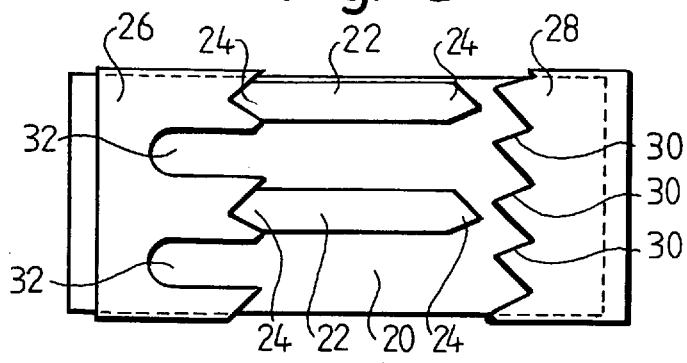
FIGS. 2a–2d respectively show a portion of the first embodiment of the affixing device according to the invention in different stages of affixing.
Figure 2B:
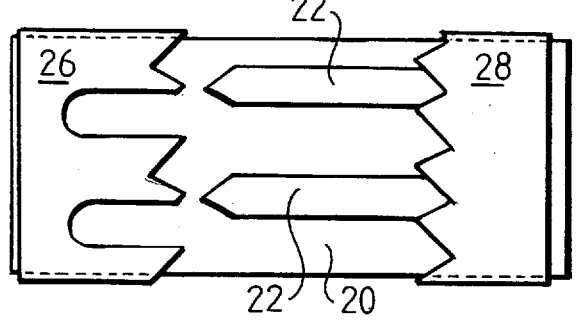
Figure 2C:
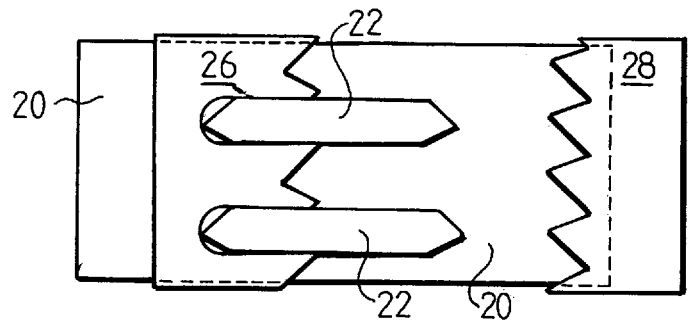

FIGS. 1a–1d show the invention according to a first preferred embodiment. To facilitate description of the invention, the affixing device is shown in two parts (FIGS 1a and 1b) and two cross sections (I—I in FIG. 1c and II—II in FIG. 1d).

The affixing device contains an elongate, preferably tubular, connector part 4 with an opening 6 through which a contact pin 8 can be inserted for affixing the connector part 4. The connector part has an opening collar 10, projecting into a tubular middle part 12, formed by two parts, a first section 14, nearest the opening collar 10, which forms a space in the connector part 4, in the shape of a truncated cone with the smaller diameter pointing toward the opening 6, and a second section 16, which forms a cylindrical space connected to the conical space. The cylindrical space formed by the second section of the middle part 12 merges into an additional cylindrical space formed by an inner part 18 which caps the connector part 4.

A cylindrical, movably arranged guide body 20 is inside the cylindrical space formed by the second section 16. The length of the guide body 20 is approximately the same as the length of the second section 16. The surface of the guide body 20 has a number, preferably 6–8, of longitudinal, rib-like projections 22 running parallel to the longitudinal direction of the guide body 20 and extending along part of the its length. These projections 22 preferably have a rectangular profile. The tips 24 of the projections 22 have one steeply angled side and one shallowly angled side on either side of the tip.

An outer tubular guide 26 is arranged inside the middle part 12, where the first section 14 merges into the second section 16, and encircles the outer part of the guide body 20. An inner tubular guide 28, encircling the inner part of the guide body 20, is mounted at the point at which the second section 16 merges to the space formed by the inner part 18.

The inner guide 28 has a number of identical notches 30 arranged on the part facing the opening 6. These notches have an steeply angled side and a shallowly angled side arranged to mesh with the corresponding steeply angled and shallowly angled sides of the tips 24 of the projections on the guide body 20.

The outer guide 26 has a number of notches 30,32 arranged on the part facing away from the opening 6. Notches 32 which are deeper alternated with notches 30 which are shallower. The shallow notches 30 have a steeply angled side and a shallowly angled side arranged to mesh with the corresponding steeply angled and shallowly angled sides of the projections on the guide body 20.

The inner guide 28 and outer guide 26 respectively have the same number of notches, whose number is equal to twice the number of projections 22 on the guide body 20.

As a result of their interaction with the inner and outer guides 28 and 26, the projections 22 on the guide body 20 limit the guide body's movement in the connector part's longitudinal direction.

A tensioned main spring 34 is arranged between the guide body 20 and the cap on the inner part 18 and presses the guide body 20 toward the opening G. As a result of the spring force, the projections 22 on the guide body 20 push against the notches 30 and 32 in the outer guide 26.

Because of the spring force, the guide body 20 pushes against the affixing part 36 arranged in the conical space formed by the first section 14 of the middle part 12. The affixing part 36 has a concentricity located opening 38 for admitting the contact pin.

Referring to FIGS. 2a–2d, the function of the affixing device according to the first preferred embodiment will now be explained.

FIG. 2a shows the guide body 20 and the inner and outer guides 28 and 26. As a result of the spring force, the tips 24 of the projections 22, with their steeply angled and shallowly angled sides, push against the shallow notches 30 in the outer guide 26. When a contact pin (not shown) is inserted into the connector part, it causes the guide body 20 to be pushed back toward the inner guide 28 until the shallowly angled sides of the projections meet the corresponding shallowly angled sides on the inner guide 28, forcing the control body 20 to rotate (downwardly) until the tips 24 of the projections 22 bottom in the notches 30 of the inner guide 28 (see FIG. 2b). When the force, exerted by the contact pin along the connector part against the spring 34 terminates, the main spring 34 pushes the guide body 20 back so the projections are pushed down, because the guide body 20 has rotated, into the deep notches 32 in the outer guide 26. When the projections 22 are seated in the deep notches 32, the affixing part 36 is pushed toward the opening collar 10, and the affixing part 36, as a result of the conical shape of the opening collar 10, is pushed in toward the connector part's center axis, thereby exerting an affixing force on the contact pin which is accordingly secured in the connector part.

Figure 2D:
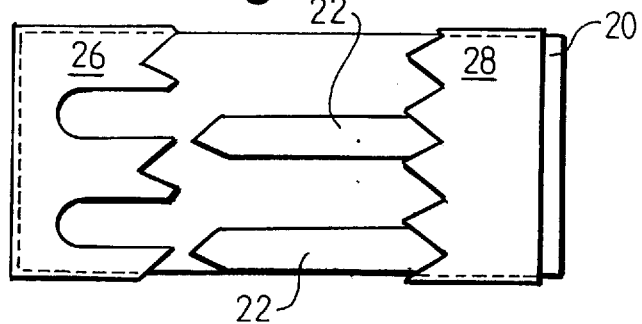

When the contact pin is to be detached (see FIG. 2c), force is applied to the contact pin against the connector part, causing the guide body 20 to push back against the inner guide 28 until the shallowly angled sides of the projections 22 meet the corresponding shallowly angled sides of the inner guide 28, forcing the guide body 20 to rotate (downwardly) until the tips 24 of the projections 22 bottom in the notches of the inner guide 28 (see FIG. 2d). When the force exerted by the contact pin along the connector part against the main spring 34 terminates, the main spring 34 pushes the guide body 20 back so the projections are pushed down, because the guide body 20 has rotated, down into the shallow notches 30 in the outer guide 26.

When the projections 22 are seated in the shallow notches 30 in the outer guide 26, the affixing part no longer presses against the opening collar 10 and is accordingly unable to exert any affixing force on the contact pin. The contact pin can therefore be detached.

As noted above, the affixing part has an opening 38 to admit a contact pin, this opening 38 continuing a distance into the guide body 20. The affixing part has a number, e.g. four, of preferably wedge-shaped clamping sections 40 designed, e.g. by the use of longitudinal slots, to make the clamping sections sufficiently radially mobile so as to clamp and hold the contact pin when acted upon by the spring force.

FIGS. 3a–3d show an alternative design for the first preferred embodiment of the affixing device according to the invention. According to the above-described embodiment, the contact pin actuates the guide body 20 by pushing directly against it. In order to achieve this, the contact pin must have a minimum length. According to the alternative shown in FIGS. 3a–3d, an isolation flange 42, which is arranged near the contact pin, is instead made to push against an outer collar 44 which, in turn, presses against the affixing part 36. Affixing and releasing the contact pin are performed in the same way as was described above. The advantage of this alternative version of the first preferred embodiment is that it operates regardless of the length of the contact pin, since it is the isolation flange 42, not the contact pin, which acts on the affixing part and guide body. A stop 46 is arranged near the outer collar 44 to keep the collar from being pulled off. Two cross-sectional views (III—III in FIG. 3c, IV—IV in FIG. 3d) of the affixing device are shown.

In the first preferred embodiment, electrical contact with the contact pin can be established in different ways, e.g. via the opening collar 10 and the clamping sections on the affixing part 40, to the contact pin or via the inner part 18, main spring 34, guide body 20 and the affixing part's clamping sections 40 to the contact pin B.

FIG. 4a–4d show a side view of the affixing device of the invention according to a second preferred embodiment in different stages of contact pin-affixing. In the description of the second embodiment, the parts which functionally correspond to parts in the first preferred embodiment have been assigned the same names and reference designations.

Figure 4A:
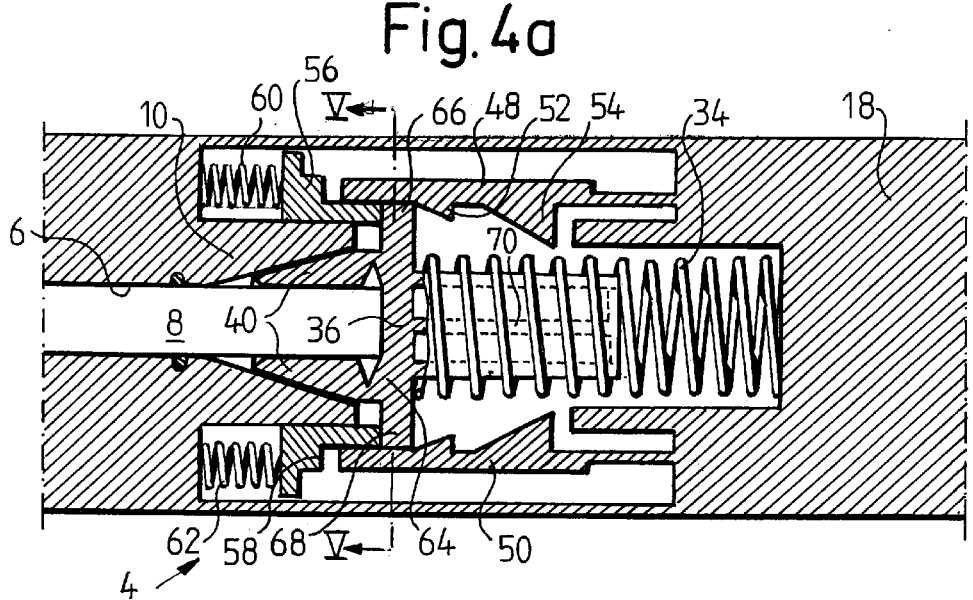
FIGS. 4a–4d respectively show a portion of the second embodiment of the affixing device according to the invention in different stages of affixing.
Figure 5:
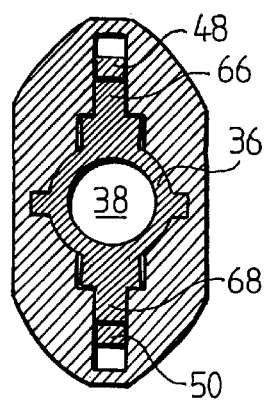
FIG. 5 shows a cross section of the second embodiment of the affixing device according to the invention.
Figure 4C:
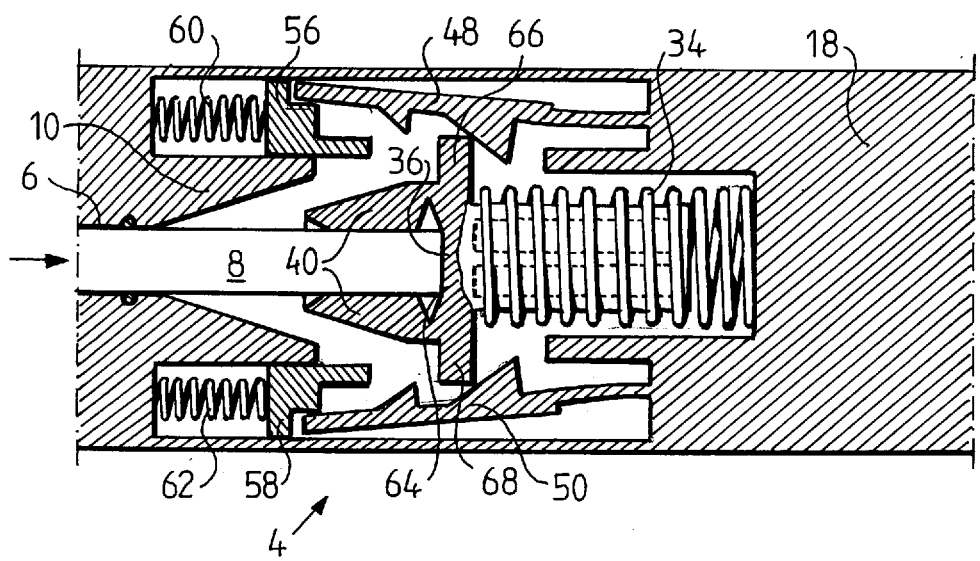
Figure 4D:
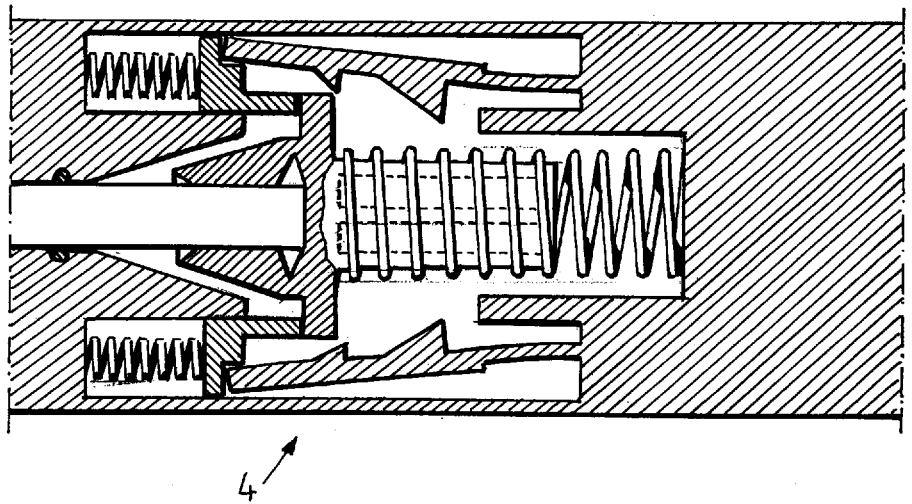

Thus, this second embodiment of the affixing device has a connector part 4 which can have an oval cross section, as shown in FIG. 5 which shows a section I—I from FIG. 4a. In a similar manner as in the first embodiment, the connector part 4 has an opening collar 10 with an opening 6 through which a contact pin 8, which is to be secured, is inserted into the connector part 4. The opening 6 merges to a conical space which, in turn, merges into a substantially cylindrical space formed by an inner part. First and second blocking part 48 and 50 extend from this inner part along the longitudinal axis-of the connector part towards the opening. Two cavities are formed by the blocking parts 48 and 50 and the outer wall of the connector part 4 above and below the blocking parts 48 and 50. When actuated, the blocking parts 48 and 50 are bent into these cavities. First and second wedge-shaped blocking catches 52 and 54 facing the center axis of the connector part 4, are arranged on the blocking parts 48 and 50. Each blocking catch 52 and 54 has one sloping edge facing the opening and one radially extending edge facing away from the opening. The second catch 54 is about twice as high as the first catch 52. The first catch 52 is located nearest the opening.

The blocking parts 48 and 50 interact with two gauge blocks, first and second gauge blocks 56 and arranged on the blocking parts 48 and 50 toward the opening. The gauge blocks 56 and 58 are acted upon by first and second springs 60 and 62 in a direction away from the opening and parallel to the longitudinal axis of the connector part, toward the blocking parts 48 and 50.

The connector part has an affixing part 36, with an opening 38 for the contact pin, movably arranged in the connector part's longitudinal direction. The affixing part 36 has a wedge-shaped, clamping section 40 nearest the opening, a guide 64 with first and second parts 66 and 68 and a tubular capping section 70.

A main spring 34 is arranged in the tensioned state in the inner part 18 between the rear wall of the inner part, partially encircling the tubular section 70 of the affixing part and pressing against the affixing part's guide 64.

FIG. 4a shows the contact pin secured by the affixing device according to the invention. The main spring 34 presses against the guide 64 and pushes the clamping section 40 into the conical space. The guide's first and second parts 66 and 68 push against the first and second gauge blocks 56 and 58 respectively, which are pushed back, since the first and second springs 60 and 62 jointly exert much less force than the main spring 34. The clamping section 40 is so flexible that it applies a radial-affixing force to the contact pin, when the pin is inserted into the conical space, thereby affixing the pin in the connector part.

When the contact pin is detached, a force, directed into the connector part, is applied to the contact pin, the affixing part 36 then being displaced, and the guide's first and second parts 66 and 68 cause the first and second blocking parts 48 and 50, when contacting the first blocking catches 52, to bend outward in the cavities until the guide passes the catches 52, and the blocking parts 48 and 50 rebound. The affixing part is now held in place by the first blocking catches 52, and the clamping force exerted by the clamping sections ceases, making it possible for the contact pin to be withdrawn (see FIG. 4b).

Figure 4B:
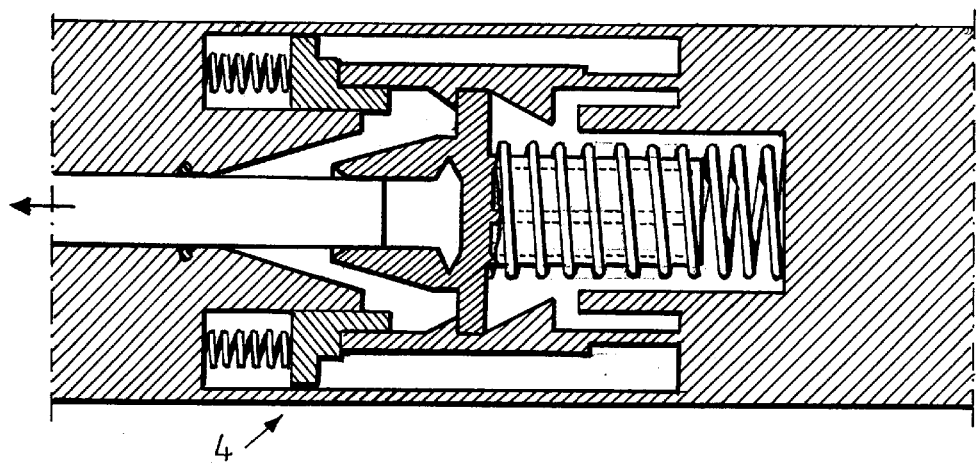

In affixing the contact pin, the starting point is shown in FIG. 4b. The contact pin 8 is inserted into the connector part (see FIG. 4c), pressing the affixing part 36 against the main spring 34. The guide's first and second parts 66 and 68 cause the blocking parts 48 and 50, via the second blocking catches 54, to bend outwardly, and the gauge blocks 56 and 58, in a position near the connector part's outer wall, can, due to the force exerted by the first and second springs 60 and 62, move into the connector part and hold the blocking parts 48 and 50 in the bent-out position, as they rest on recesses in the gauge blocks 56 and 58. Since the blocking parts 48 and 50 are in this bent-out position, the guide 64, due to the force exerted by the main spring 34, can move toward the opening, and the guide's first and second sections 66 and 68 can pass the first blocking catches (see FIG. 4d). The guide's first and second parts 66 and 68 move the gauge blocks 56 and 58 toward the opening, parallel to the connector part's longitudinal axis, and the blocking parts 48 and 50 return to their normal position (see FIG. 4a). This secures the contact pin as described above.

Electrical contact with the contact pin in the second preferred embodiment can be established in different ways, analogous to the method used for the first embodiment, e.g. via the opening collar 10 and the clamping sections of the affixing part 40 to the contact pin 8 or via the internal part 18 of the connector part, the main spring 34 and the clamping sections of the affixing part 40 to the contact pin 8.

Although modifications and changes may be suggested by those skilled in the art, it is the intention of the inventor to embody within the patent warranted hereon all changes and modifications as reasonably and properly come within the scope of his contribution to the art.

I claim as my invention:

1. A contact pin affixing device comprising:

an electrically conductive contact pin;

a housing containing a connector part having an opening with a longitudinal axis, said contact pin being inserted into said opening in a direction along said longitudinal axis; and an affixing assembly, contained in said connector part and through which said contact pin passes as said contact pin moves along said longitudinal axis, said affixing assembly having elements actuated exclusively by longitudinal movement of said contact pin to move between a contact pin-affixing position and a contact pin-release position, at least one of said elements being electrically conductive and producing an electrical connection with said contact pin in said pin-affixing position.

2. A device as claimed in claim 1 wherein said contact pin is in an affixed position when said elements are in said contact pin-affixing position, and wherein said affixing assembly comprises means, actuated by movement of said contact pin into said opening by a predetermined distance into said connector part beyond said affixed position, for moving said elements from said contact pin-affixing position to said contact pin-release position.

3. A device as claimed in claim 1 wherein said affixing assembly comprises at least two clamping sections mounted for inward clamping movement toward said contact pin as said contact pin passes said clamping sections during insertion to push against said contact pin in said contact pin-affixing position, and a spring disposed in said connector part and mechanically connected to said clamping sections for exerting a force along said longitudinal direction toward said opening in said connector part.

4. A device as claimed in claim 3 wherein said connector part contains blocking means for, when said elements are in said contact pin-release position, locking said clamping sections in a position out of contact with said contact pin.

5. A device as claimed in claim 4 wherein said connector part comprises a cylindrical guide body pushing against said spring and movably mounted in said connector part for acting on said affixing assembly, said guide body having a plurality of rib-like longitudinal projections, inner and outer tubular gauge blocks disposed in said connector part with said guide body being disposed between said inner and outer tubular gauge blocks, said projections of said guide body mechanically interacting with said gauge blocks and alternatingly locking said gauge blocks in said contact pin-affixing position and said contact pin-release position.

6. A device as claimed in claim 5 wherein said projections on said guide body extend parallel to said longitudinal axis and wherein each projection has a rectangular cross section and tips respectively disposed at opposite ends of said projections, each tip having a sharply angled side and a shallowly angled side, and wherein said gauge blocks each have a plurality of notches disposed to respectively engage said tips of said projections.

7. A device as claimed in claim 4 wherein said connector part comprises two opposed blocking parts mounted to mechanically interact with said affixing assembly for alternatingly locking said fixing assembly in said contact pin-release position against a force exerted by said spring and to release said affixing assembly from said contact pin-release position to move said affixing assembly into said contact pin-affixing position.

8. A device as claimed in claim 7 wherein each blocking part comprises first and second wedge-shaped blocking catches respectively facing a center axis of said connector part, each blocking catch having a sloping edge facing said opening and a radially extending edge facing away from said opening, said second blocking catch having a height which is substantially twice as high as a height of said first blocking catch, said first blocking catch being disposed nearer said opening, and said blocking catches being disposed for interacting with said affixing assembly when said elements move between said contact pin-affixing position and said contact pin-release position, said first blocking catches pressing against and being locked to said affixing assembly in said contact pin-release position and said affixing assembly, when moving to said contact pin-affixing position, causing said second blocking catches to detach said affixing assembly from said first blocking catches.

* * * * *